United States Patent [19]

Isogai et al.

[11] 4,451,678

[45] May 29, 1984

[54] PROCESS FOR PRODUCING ETHANOL

[75] Inventors: Nobuo Isogai; Motoyuki Hosokawa; Takashi Okawa; Natsuko Wakui; Toshiyasu Watanabe, all of Niigata, Japan

[73] Assignee: Agency of Industrial Science and Technology, Tokyo, Japan

[21] Appl. No.: 484,267

[22] Filed: Apr. 12, 1983

[30] Foreign Application Priority Data

Apr. 16, 1982 [JP] Japan ................................. 57-62345

[51] Int. Cl.³ ........................ C07C 31/08; C07C 29/00
[52] U.S. Cl. .................................... 568/902; 568/877; 568/885; 568/907
[58] Field of Search ......................................... 568/902

[56] References Cited

U.S. PATENT DOCUMENTS 4,304,946 12/1981 Isogai et al. ......................... 260/902

Primary Examiner—J. E. Evans
Attorney, Agent, or Firm—Browdy and Neimark

[57] ABSTRACT

A process for producing ethanol which comprises reacting methanol, carbon monoxide and hydrogen in the presence of (a) a catalyst comprising cobalt or a cobalt compound and an alkyl phosphine as an effective component and (b) a co-catalyst comprising hydrochloric acid and in the absence of an iodide is disclosed. According to the present invention, formation of by-products becomes less and selectivity to realizable ethanol becomes higher.

9 Claims, No Drawings

PROCESS FOR PRODUCING ETHANOL

BACKGROUND OF THE INVENTION

This invention relates to a process for producing ethanol from methanol, carbon monoxide and hydrogen.

It was known in the prior art that ethanol was produced from methanol, carbon monoxide and hydrogen by using a catalyst comprising a cobalt salt as a main component and iodine, or an iodine compound and optionally a ruthenium compound or an osmium compound. According to this prior methods, many by-products, such as dimethyl ether, methyl ethyl ether, diethyl ether, acetaldehyde, dimethoxy ethane, acetic acid, methyl acetate, ethyl acetate, methyl formate and compounds having $C_3$ or more were produced together with ethanol. That is, selectivity to neat ethanol was insufficient in the prior method, and complicated steps were necessary for separating ethanol from the reaction mixture.

Recently, it has been proposed to add a variety of ligands, such as tertiary phosphine, tertiary arsines or tertiary antimony to the prior catalyst for producing ethanol from methanol, carbon monoxide and hydrogen. For example, British Pat. No. 1,546,428 discloses a process for producing ethanol by reacting methanol, carbon monoxide and hydrogen in a hydrocarbon solvent in the presence of the catalyst composed of cobalt-iodine or bromide-tertiary phosphine. There is the passages "ratio of cobalt (gram-atom) to phosphine (mol) is 1:2–1:4" and "ratio of iodide or bromide (gram-atom) to phosphine (mol) is 1:1–1:2" in the claims of the British Patent. British Pat. No. 2,036,739 discloses a process for producing ethanol by reacting methanol, carbon monoxide and hydrogen in the presence of a catalyst composed of cobalt and ruthenium or osmium, promoter composed of a tertiary phosphine and an iodide in which ratio of the iodide to cobalt is 3:1–1:10.

The present inventors found that when methanol reacts with CO and $H_2$ in the presence of combination of ligands, such as a tertiary phosphine, and large amount of iodide, by-products, such as acetaldehyde, dimethoxy ethane and high boiling point products which are not detectable by gas chromatograph are formed, so selectivity to neat ethanol is not necessarily high.

SUMMARY OF THE INVENTION

The present inventors carried out research for overcoming the shortcomings mentioned above. As a result, we found that when methanol reacts with carbon monoxide and hydrogen in the presence of (a) a catalyst comprising a cobalt or a cobalt compound and an alkyl phosphine as a main component and (b) a co-catalyst comprising hydrochloric acid and in the absence of an iodide, formation of by-products is reduced remarkably and neat ethanol is produced in high selectivity to ethanol.

This invention relates to a process for producing ethanol which comprises reacting methanol, carbon monoxide and hydrogen in the presence of (a) a catalyst comprising a cobalt or a cobalt compound and an alkyl phosphine as an effective component, and (b) a co-catalyst comprising hydrochloric acid and in the absence of an iodide.

According to the present invention, it is critical that cobalt or a cobalt compound, an alkyl phosphine and hydrochloric acid coexist in the reaction system. When only one or two of the three components exist in the reaction system, selectivity to ethanol becomes lower.

The cobalt compounds include, for example, cobalt carbonyls, such as dicobalt octacarbonyl and cobalt hydride tetracarbonyl. Synthetic solutions obtained by reacting an inorganic cobalt compound, such as cobalt hydroxide, cobalt carbonate, basic cobalt carbonate or cobalt chloride, or an organic cobalt compound, such as a cobalt organic acid salt, cobaltocene or cobalt acetyl acetonate with synthesis gas containing $H_2$ and CO in methanol, or synthesis solutions obtained by reacting the inorganic cobalt compound or the organic cobalt compound with synthesis gas in the presence of a tertiary phosphine and a hydrocarbon solvent or an ether solvent can also be used as the cobalt compound constituting the catalyst. However, the cobalt compounds exclude cobalt iodide and cobalt bromide. The cobalt compound may be used alone or as a mixture. Dicobalt octacarbonyl is preferable.

The amount of the cobalt compound employed is in the range of 1–300 mg-atom, preferably 5–100 mg-atom in terms of cobalt per 1 mol of methanol. When the amount of cobalt compound is less than the lower limit mentioned above, though the reaction proceeds, the reaction speed is lowered. The use of cobalt compound in an amount of more than the upper limit merely adds to production cost.

Concentration of hydrochloric acid employed in the reaction system is not critical. However, preferably the concentration of hydrochloric acid is more than 1% by weight. Preferably use of hydrochloric acid in an amount of less than the above limit lowers the space time yield of ethanol. The amount of hydrochloric acid employed may be in the range of 0.01–2 gram-atom per 1 gram-atom of cobalt, and more preferably 0.05–1 gram-atom per 1 gram-atom of cobalt.

The alkyl phosphines of the present invention include, for example, tri-n-butyl phosphine, triphenyl phosphine, tri-p-tolylphosphine, tricyclohexyl phosphine, 1,4-bisdiphenyl phosphinobutane and 1,6-bis-diphenyl phosphinohexane. Tri-n-butyl phosphine is preferable.

The amount of the alkyl phosphine employed is in the range of 2–600 mg-atom, preferably 10–200 mg-atom in terms of phosphorus per 1 mol of methanol. The use of the tertiary phosphine in an amount of less than the lower limit as mentioned above is less effective for suppressing formation of esters or ethers. The use of tertiary phosphine in an amount of more than the upper limit lowers the reactivity of the methanol and selectivity to ethanol.

The atomic ratio of cobalt:hydrochloric acid (in terms of chlorine):phosphorus in the catalyst of this invention may be in the range of 1:from 0.01 to 2:from 0.1 to 2 and preferably 1:from 0.05 to 1:from 0.5 to 1.8. The catalysts with proportions outside the above ranges increase formation of by-products, such as ethers, esters and high boiling point products.

Use of solvent is not critical in this invention. However, the reaction may be carried out in the presence of solvents which do not give a bad effect on the reaction.

The solvents which are inert to the reaction system include hydrocarbons, ethers and esters. Hydrocarbon solvents include, for example, aromatic hydrocarbons, such as toluene, benzene and xylene; aliphatic hydrocarbons, such as hexane and octane; and alicyclic hydrocarbons, such as cyclohexane. The ether solvents include, for example, diethyl ether, diiopropyl ether, dioxane and tetrahydrofuran. The ester solvents include methyl acetate and ethyl acetate. The solvent may be used alone or as a mixture. Toluene is preferable.

The amount of the solvent employed may be in the range of 0.01–5 mol, preferably 0.1–2 mole per 1 mol of methanol. Use of solvent in an amount of more than the above upper limit lowers the space time yield of ethanol and is not practical.

The reaction temperature depends on the catalyst employed and other reaction conditions. In general, the temperature may be in the range of 150°–300° C., preferably 200°–260° C. Though the reaction proceeds at a temperature below 150° C., the reaction speed is low; at temperatures above 300° C. by-products forms.

The reaction pressure may be in the range of more than 50 kg/cm², and preferably, the pressure is in the range of 150–450 kg/cm² in the practice of the present invention. Carbon monoxide and hydrogen may be used in an amount of more than the stoichiometric amount of methanol. The molar ratio of CO to $H_2$ employed may be in the range of 4:1 to 1:4, preferably 2:1 to 1:3.

Carbon monoxide and hydrogen employed in the present invention may contain argon, nitrogen, carbon dioxide, methane, ethane and other inert gases. In this case, the total partial pressure of each of carbon monoxide and hydrogen is within the above reaction pressure.

The present invention can be carried out either as batch process or as a continuous process.

The present invention is further illustrated by non-limiting Examples and Comparative Run.

In the following Examples and Comparative Run, reactivity of methanol, selectivity to ethanol, substantial reactivity of methanol and selectivity to realizable ethanol are expressed by the following equations:

Reactivity of methanol (%) =

$$\frac{\text{mol of } CH_3OH \text{ fed} - \text{mol of unreacted } CH_3OH}{\text{mol of } CH_3OH \text{ fed}} \times 100$$

Selectivity to each product (%) =

$$\frac{\text{mol of } CH_3OH \text{ converted to each product}}{\text{mol of } CH_3OH \text{ fed} - \text{mol of unreacted } CH_3OH} \times 100$$

Substantial reactivity of methanol (%) =

$$\frac{\text{mol of } CH_3OH \text{ fed} - \text{mol of unreacted } CH_3OH - \text{mol of } CH_3OH \text{ converted}^{*1}}{\text{mol of } CH_3OH \text{ fed}} \times 100$$

Selectivity to realizable ethanol (%) =

$$\frac{\text{mol of } CH_3OH \text{ converted to realizable } C_2H_5OH^{*2}}{\text{mol of } CH_3OH \text{ fed} - \text{mol of unreacted } CH_3OH - \text{mol of } CH_3OH \text{ converted}} \times 100$$

*[1] contains components, such as dimethoxy methane, methyl esters,

EXAMPLE 1

Into a shaking type 100 ml autoclave made of stainless steel were charged 10 gram (g) (0.3121 mol) of methanol, 2 g (0.0058 mol) of dicobalt octacarbonyl, 0.4 g (0.004 mol) of 36% hydrochloric acid solution, and 3 g (0.0148 mol) of tri-n-butyl phosphine. Mixed gas of $H_2$ and CO (molar ratio of 1:1) was fed to pressure of 200 kg/cm². The reaction was carried out at 230° C. for three hours.

After the reaction, the autoclave was cooled and the gas remaining inside the autoclave was discharged to atmospheric pressure. Gas Chromatograph (GC) Analysis (internal standard method) showed reactivity of methanol of 24.4% and selectivity to neat ethanol of 70.4%. Selectivity to each of the following components was as follows:

| | |
|---|---|
| methyl formate | 1.0% |
| methyl ethyl ether | 1.6% |
| methyl acetate | 2.0% |
| dimethoxy ethane | trace |

This shows substantial reactivity of methanol of 23.0% and selectivity to realizable ethanol of 76.4%.

EXAMPLE 2

The procedure of Example 1 was repeated except that 10 g (0.1086 mol) of toluene was added to the reaction system.

The results were as follows:

| | |
|---|---|
| reactivity of methanol | 22.0% |
| selectivity to neat ethanol | 79.5% |
| selectivity to methyl formate | 2.7% |
| selectivity to methyl ethyl ether | 1.4% |
| Selectivity to methyl acetate | trace |
| selectivity to dimethoxy ethane | trace |

This shows substantial reactivity of methanol of 21.3% and selectivity to realizable ethanol of 83.2%.

EXAMPLE 3

The procedure of Example 2 was repeated except that 10 g (0.1135 mol) of dioxane was used in place of toluene. The results were as follows:

| | |
|---|---|
| reactivity of methanol | 32.7% |
| selectivity to neat ethanol | 73.3% |
| selectivity to methyl formate | 0.7% |
| selectivity to methyl ethyl ether | 1.7% |
| selectivity to methyl acetate | 1.8% |
| selectivity to dimethoxy ethane | 2.7% |

This shows substantial reactivity of methanol of 29.5% and selectivity to realizable ethanol of 80.2%.

Comparative Runs 1-3

The procedures of Example 2 were repeated except that three component catalysts consisting of dicobalt octacarbonyl (main component of the catalyst), hydrochloric acid and tri-n-butyl phosphine and toluene as shown in Table 1 is used. The results are shown in Table 1. The lack of three component catalysts (Comparative Run) gives inferior result to use of three component catalysts (Example 2) with respect to selectivity to neat ethanol, formation of by-products, such as ethers and esters and selectivity to realizable ethanol.

TABLE 1

| | Comp. Run 1 | Comp. Run 2 | Comp. Run 3 |
|---|---|---|---|
| Co₂(CO)₈ g (mol) | 2 (0.0058) | 2 (0.0058) | 2 (0.0058) |
| 36% hydrochloric | — | 0.4 (0.004) | — |

TABLE 1-continued

|  | Comp. Run 1 | Comp. Run 2 | Comp. Run 3 |
|---|---|---|---|
| acid g (mol) |  |  |  |
| tri-n-butyl phosphine g (mol) | 3 (0.0148) | — | — |
| toluene g (mol) | 10 (0.1086) | 10 (0.1086) | 10 (0.1086) |
| reactivity of methanol % | 28.7 | 8.2 | 9.0 |
| substantial reactivity of methanol % | 26.3 | 6.0 | 6.2 |
| Selectivity to each component % ethanol | 56.3 | 24.9 | 23.4 |
| methyl formate | 7.0 | 6.6 | 18.0 |
| methyl acetate | 0.6 | 2.0 | 1.2 |
| methyl ethyl ether | 2.7 | 7.3 | 8.6 |
| dimethoxy ethane | — | — | — |
| realizable ethanol | 63.3 | 31.5 | 36.9 |

Comparative Runs 4 and 5

The procedures were repeated as in Example 2 except that cobalt iodide was used in place of dicobalt octacarbonyl (Comparative Run 4), or 57 percent iodic acid was used in place of hydrochloric acid (Comparative Run 5), and the reaction time was one hour and the reaction temperature was 200° C. The results are shown in Table 2. The results show that presence of iodic acid increases by-products, such as acetaldehyde and dimethoxy ethane and lowers selectivity to neat ethanol.

TABLE 2

|  |  | Comp. Run 4 | Comp. Run 5 |
|---|---|---|---|
| cobalt catalyst g (mol) |  | CoI$_2$ 1 (0.0032) | Co$_2$(CO)$_8$ 2 (0.0058) |
| co-catalyst g (mol) |  | HCl 0.4 (0.004) | HI 0.88 (0.004) |
| tri-n-butyl phosphine g (mol) |  | 3 (0.0148) | 3 (0.0148) |
| toluene g (mol) |  | 10 (0.1086) | 10 (0.1086) |
| reactivity of methanol % |  | 57.6 | 30.3 |
| substantial reactivity of methanol % |  | 39.4 | 25.4 |
| selectivity to each component | ethanol | 19.1 | 47.8 |
|  | acetaldehyde | 14.2 | 1.3 |
|  | methyl acetate | 3.6 | 2.1 |
|  | methyl ethyl ether | 1.1 | 3.3 |
|  | dimethoxy ethane | 43.5 | 18.1 |

TABLE 2-continued

|  | Comp. Run 4 | Comp. Run 5 |
|---|---|---|
| % realizable ethanol | 69.4 | 67.6 |

Comparative Run 6

The procedure of Example 2 was repeated except that 2.8 g (0.0116 mol) of cobalt chloride hexahydrate was used in place of dicobalt octacarbonyl and hydrochloric acid. The results were as follows:

| reactivity of methanol | 36.7% |
|---|---|
| selectivity to neat ethanol | 37.2% |
| selectivity to methyl formate | 2.0% |
| selectivity to methyl ethyl ether | 5.4% |
| selectivity to methyl acetate | 5.4% |
| selectivity to dimethoxy ethane | 2.6% |

This shows substantial reactivity of methanol of 29.8% and selectivity to realizable ethanol of 58.2%.

What is claimed is:

1. A process for producing ethanol which comprises reacting methanol, carbon monoxide and hydrogen in the presence of (a) a catalyst comprising cobalt or a cobalt compound and an alkyl phosphine as an effective component and (b) a co-catalyst comprising hydrochloric acid and in the absence of an iodide.

2. The process as defined in claim 1 wherein the cobalt compound is dicobalt octacarbonyl.

3. The process as defined in claim 1 wherein the alkyl phosphine is tri-n-butyl phosphine.

4. The process as defined in claim 1 wherein the reaction is carried out in the presence of toluene.

5. The process as defined in claim 4 wherein the solvent is toluene.

6. The process as defined in claim 4 wherein solvent is used in an amount of 0.01–5 mol per 1 mol of methanol.

7. The process as defined in claim 1 wherein carbon monoxide and hydrogen are used in an amount of more than the stoichiometric amount of methanol.

8. The process as defined in any one of claims 1–7 wherein the reaction pressure is in the range of 50–450 kg/cm$^2$.

9. The process as defined in any one of claims 1–7 wherein the reaction temperature is in the range of 150°–300° C.

* * * * *